United States Patent [19]
Kelleher et al.

[11] Patent Number: 5,674,889
[45] Date of Patent: Oct. 7, 1997

[54] AROMATIC COMPOUNDS, COMPOSITIONS CONTAINING THEM AND THEIR USE IN THERAPY

[75] Inventors: Fintan Kelleher; Richard Thomas Lewis; Angus Murray Macleod, all of Harlow, United Kingdom

[73] Assignee: Merck, Sharp & Dohme, Ltd., Hoddesdon, England

[21] Appl. No.: 513,759

[22] PCT Filed: Feb. 15, 1994

[86] PCT No.: PCT/EP94/00438

§ 371 Date: Aug. 21, 1995

§ 102(e) Date: Aug. 21, 1995

[87] PCT Pub. No.: WO94/19320

PCT Pub. Date: Sep. 1, 1994

[30] Foreign Application Priority Data

Feb. 22, 1993 [GB] United Kingdom ............ 9303540
Feb. 25, 1993 [GB] United Kingdom ............ 9303843

[51] Int. Cl.⁶ ............ A61K 31/405; C07D 209/10; C07D 209/14
[52] U.S. Cl. ............ 514/419; 514/415; 548/495; 548/496; 548/506; 548/507
[58] Field of Search ............ 548/507, 495, 548/496, 506; 514/419, 415, 621, 625, 627

[56] References Cited

U.S. PATENT DOCUMENTS 5,328,927 7/1994 Lewis et al. ............ 514/415
5,472,978 12/1995 Baker et al. ............ 514/443

FOREIGN PATENT DOCUMENTS 0 482 539 A2 4/1992 European Pat. Off.
WO93/01169 1/1993 WIPO
WO93/18023 9/1993 WIPO
WO94/01402 1/1994 WIPO

OTHER PUBLICATIONS

Vaught JF. Life Science. 43 (18) 1419–1431. 1988.

Primary Examiner—C. Warren Ivy
Assistant Examiner—Evelyn Huang
Attorney, Agent, or Firm—Robert J. North; Melvin Winokur

[57] ABSTRACT

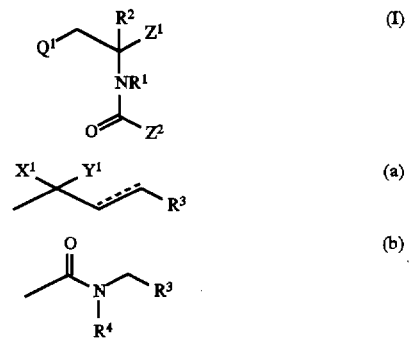

The present invention relates to compounds of formula (I) and salts and prodrugs thereof, wherein $Q^1$ represents a phenyl group substituted by one or more halo optionally substituted naphthyl, optionally substituted indolyl, optionally substituted benzthiophenyl, optionally substituted benzofuranyl, optionally substituted benzyl or optionally substituted fluorenyl; $R^1$ represents H or $C_{1-6}$alkyl; $R^2$ represents H, $C_{1-6}$alkyl or $C_{2-6}$alkenyl; $Z^1$ represents a group selected from (a) or (b). The compounds are tachykinin antagonists useful for treating pain or inflammation, migraine or emesis.

15 Claims, No Drawings

AROMATIC COMPOUNDS, COMPOSITIONS CONTAINING THEM AND THEIR USE IN THERAPY

This application is the national phase of PCT/EN94/00438, filed Feb. 15, 1994.

This invention relates to a class of heterocyclic compounds, which are useful as tachykinin receptor antagonists.

The tachykinins are a group of naturally-occurring peptides found widely distributed throughout mammalian tissues, both within the central nervous system and in the peripheral nervous and circulatory systems. The structures of three known mammalian tachykinins are as follows:

Substance P:
Arg-Pro-Lys-Pro-Gln-Gln-Phe-Phe-Gly-Leu-Met-$NH_2$
Neurokinin A:
His-Lys-Thr-Asp-Ser-Phe-Val-Gly-Leu-Met-$NH_2$
Neurokinin B:
Asp-Met-His-Asp-Phe-Phe-Val-Gly-Leu-Met-$NH_2$ Substance P is believed inter alia to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Symposium 91, 13–34 (published by Pitman) and Otsuka and Yanagisawa, "Does Substance P Act as a Pain Transmitter?" TIPS (December 1987) 8 506–510], specifically in the transmission of pain in migraine (B. E. B. Sandberg et al, J. Med Chem, (1982) 25 1009) and in arthritis [Levine et al in Science (1984) 226 547–549]. These peptides have also been implicated in gastrointestinal (GI) disorders and diseases of the GI tract such as inflammatory bowel disease [Mantyh et al in Neuroscience (1988) 25 (3) 817–37 and D. Regoli in "Trends in Cluster Headache" Ed. Sicuteri et al Elsevier Scientific Publishers, Amsterdam (1987) page 85)] and emesis [F. D. Tattersall et. al., Eur. J. Pharmacol., (1993) 250, R5–R6]. It is also hypothesised that there is a neurogenic mechanism for arthritis in which substance P may play a role [Kidd et al "A Neurogenic Mechanism for Symmetrical Arthritis" in The Lancet, 11 November 1989 and Grönblad et al "Neuropeptides in Synovium of Patients with Rheumatoid Arthritis and Osteoarthritis" in J. Rheumatol. (1988) 15(12) 1807–10]. Therefore, substance P is believed to be involved in the inflammatory response in diseases such as rheumatoid arthritis and osteoarthritis [O'Byrne et al in Arthritis and Rheumatism (1990) 33 1023–8]. Other disease areas where tachykinin antagonists are believed to be useful are allergic conditions [Hamelet et al Can. J. Pharmacol. Physiol. (1988) 66 1361–7], immunoregulation [Lotz et al Science (1988) 241 1218–21 and Kimball et al, J. Immunol. (1988) 141 (10) 3564–9], vasodilation, bronchospasm, reflex or neuronal control of the viscera [Mantyh et al, PNAS (1988) 85 3235–9] and, possibly by arresting or slowing β-amyloid-mediated neurodegenerative changes [Yankner et al, Science (1990) 250, 279–82], in senile dementia of the Alzheimer type, Alzheimer's disease and Down's Syndrome.

Tachykinin antagonists may also be useful in the treatment of small cell carcinomas, in particular small cell lung cancer (SCLC) [Langdon et. al., Cancer Research (1992) 52, 4554–7].

Substance P may also play a role in demyelinating diseases such as multiple sclerosis and amyotrophic lateral sclerosis [J. Luber-Narod et. al., poster presented at C.I.N.P. XVIIIth Congress, 28th Jun 2nd Jul., 1992] and in disorders of bladder function such as bladder detrusor hyper-reflexia (Lancet, 16th May, 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosis (European patent specification no. 0 436 334), ophthalmic disease such as conjuctivitis, vernal conjunctivitis, and the like, and cutaneous diseases such as contact dermatitis, atropic dermatitis, urticaria, and other eczematoid dermatitis (European patent specification no. 0 394 989).

In view of their metabolic instability, peptide derivatives are likely to be of limited utility as therapeutic agents. It is for this reason that non-peptide tachykinin receptor antagonists are sought.

In essence, this invention provides a class of potent non-peptide tachykinin receptor antagonists. By virtue of their non-peptide nature, the compounds of the present invention do not suffer from the shortcomings, in terms of metabolic instability, of known peptide-based tachykinin receptor antagonists.

The present invention provides a compound of formula (I), or a salt or prodrug thereof:

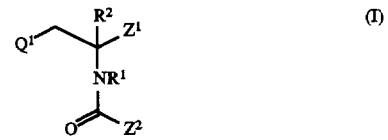

wherein
$Q^1$ represents a phenyl group substituted by one or more halo, optionally substituted naphthyl, optionally substituted indolyl, optionally substituted benzthiophenyl, optionally substituted benzofuranyl, optionally substituted benzyl, or optionally substituted fluorenyl;

$R^1$ represents H or $C_{1-6}$alkyl;

$R^2$ represents H, $C_{1-6}$alkyl or $C_{2-6}$alkenyl;

$Z^1$ represents a group selected from

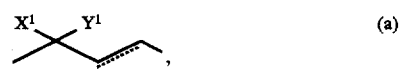

or

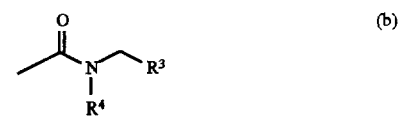

where one of $X^1$ and $Y^1$ represents H and the other represents hydroxy or $C_{1-6}$alkoxy, or $X^1$ and $Y^1$ together form a group =O or =$NOR^5$ where $R^5$ is H or $C_{1-6}$alkyl;

$R^3$ represents phenyl optionally substituted by 1, 2 or 3 groups selected from $C_{1-6}$alkyl, $C_{1-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ independently represent H, $C_{1-6}$alkyl, phenyl or trifluoromethyl;

$R^4$ represents H or $C_{1-6}$alkyl;

the dotted line represents an optional covalent bond; and when $Z^1$ represents a group of formula (a), $Z^2$ represents $C_{1-6}$alkyl$CO_2H$, phenyl or phenyl$C_{1-4}$alkyl, wherein each phenyl moiety is substituted by $CO_2H$; and when $Z^1$ represents a group of formula (b), $Z^2$ represents a group of the formula —$X^2$—$Y^2$—$R^6$; where $X^2$ represents a bond, O, S or $NR^7$, where $R^7$ is H or $C_{1-6}$alkyl;

$Y^2$ represents a bond or $C_{1-6}$alkylidene; and $R^6$ represents $NR^cR^d$ (where $R^c$ and $R^d$ each independently represent H, $C_{1-6}$alkyl, phenyl or phenyl$C_{1-4}$alkyl wherein each phenyl moiety may be substituted by one or more of $C_{1-6}$alkyl, $C_{1-6}$alkoxy, halo or trifluoromethyl) or an optionally substituted aromatic or non-aromatic azacyclic or azabicyclic group.

As used herein, the definition of each expression, when it occurs more than once in any structure, is intended to be independent of its definition elsewhere in the same structure.

The alkyl, alkenyl and alkynyl groups referred to with respect to any of the above formulae may represent straight, branched or cyclic groups or combinations thereof. Thus, for example, suitable alkyl groups include methyl, ethyl, n- or iso-propyl, n-, sec-, iso- or tert-butyl, cyclopropyl, cyclobutyl, cyclopentyl or cyclohexyl, and cycloalkyl-alkyl groups such as cyclopropylmethyl; suitable alkenyl groups include vinyl and allyl; and suitable alkynyl groups include propargyl.

For the avoidance of doubt, when the covalent bond represented by the dotted line is present, the compounds of formula (I) contain an olefinic double bond.

When $Y^2$ represents $C_{2-6}$alkylidene, it may be a straight or a branched chain.

The term "halo" as used herein includes fluoro, chloro, bromo and iodo, especially chloro and fluoro.

Where $Q^1$ represents optionally substituted fluorenyl, the group is linked through the bridgehead carbon atom, that is to say, C-9 of the fluorenyl moiety.

Where $Q^1$ represents optionally substituted naphthyl, indolyl, benzothiophenyl, benzofuranyl, benzyl or fluorenyl, suitable substituents include $C_{1-6}$alkyl, $C_{2-6}$alkenyl, $C_{2-6}$alkynyl, halo, cyano, nitro, trifluoromethyl, trimethylsilyl, $SR^a$, $SOR^a$, $SO_2R^a$, $OR^a$, $NR^aR^b$, $NR^aCOR^b$, $NR^aCOOR^b$, $COOR^a$ or $CONR^aR^b$, where $R^a$ and $R^b$ are as above defined. One or more substituents may be present and each may be located at any available ring position, except, where $Q^1$ is optionally substituted indolyl, the nitrogen atom. Where $Q^1$ is optionally substituted indolyl, suitable nitrogen substituents include $C_{1-6}$alkyl, optionally substituted phenyl($C_{1-4}$alkyl), $COOR^a$ or $CONR^aR^b$, wherein $R^a$ and $R^b$ are as above defined.

Suitable values of the group $Q^1$ include 3,4-dichlorophenyl, 3-indolyl, 2-naphthyl, 3-naphthyl, 9-fluorenyl, benzyl, 3-benzothiophenyl and 3-benzofuranyl.

Preferably $Q^1$ is 3-indolyl, 3-benzothiophenyl or 3,4-dichlorophenyl, more preferably 3-indolyl.

Suitably $R^1$ represents H or methyl, preferably H.

Preferably $R^2$ represents H or methyl, more preferably H.

Where $Z^1$ represents a group of formula (a), preferably the double bond is absent.

Suitably one of $X^1$ and $Y^1$ represents hydroxy or $C_{1-6}$alkoxy, such as methoxy, or $X^1$ and $Y^1$ together represent =O or =NOH. Preferably one of $X^1$ and $Y^1$ represents methoxy or $X^1$ and $Y^1$ together represent =O. More preferably, $X^1$ and $Y^1$ together represent =O.

When $Z^2$ represents $C_{1-6}$alkyl$CO_2H$, it will preferably represent $C_{1-3}$alkyl$CO_2H$, such as $(CH_2)_2CO_2H$.

When $Z^2$ represents phenyl substituted by $CO_2H$, substitution in the para position is preferred.

Where $Z^1$ represents a group of formula (b), preferably $R^4$ is H.

Preferably $X^2$ represents a bond, O or NH.

In one preferred subgroup of compounds according to the invention $X^2$ represents a bond and $Y^2$ represents $CH_2$.

Where $Z^1$ represents either a group of formula (a) or a group of formula (b), preferably $R^3$ represents substituted phenyl. Suitable phenyl substituents include nitro, trifluoromethyl, trimethylsilyl, bromo, chloro, fluoro, iodo, cyano, methyl, ethyl, cyclopropyl, vinyl, methoxy, phenoxy and amino. Preferably $R^3$ represents disubstituted phenyl.

Particularly preferred are compounds wherein $R^3$ represents 3,5-bis(trifluoromethyl)phenyl.

Where $Z^2$ represents a group of the formula —$X^2$—$Y^2$—$R^6$, the aromatic or non-aromatic azacycle or azabicycle $R^6$ may contain one or more additional heteroatoms selected from O and S, or groups $NR^7$, where $R^7$ is H or $C_{1-6}$alkyl, and may be unsubstituted or substituted. Suitable substituents include $C_{1-6}$alkyl, $C_{1-6}$alkoxy, oxo, SH, =S, halo, trifluoromethyl, $NR^aR^b$, $NR^aCOR^b$, $CONR^aR^b$, $CO_2R^a$ and $CH_2OR^a$, where $R^a$ and $R^b$ are as previously defined.

When $R^6$ represents $NR^cR^d$, $R^c$ and $R^d$ are suitably selected from H and $C_{1-6}$alkyl, such as $C_{1-4}$alkyl, e.g. methyl, ethyl, n-propyl, i-propyl, n-butyl, i-butyl and t-butyl.

When $R^6$ represents an aromatic azacycle or azabicycle, suitable values of $R^6$ include imidazolyl, triazolyl, tetrazolyl, oxazolyl, thiazolyl, pyrrolyl, pyrazolyl, pyrazinyl, pyridyl, oxadiazolyl, thiadiazolyl, isoxazolyl, isothiazolyl, benzimidazolyl, benzoxazolyl and indolyl, preferably imidazolyl, such as 2,4-imidazolyl, or pyridyl, more preferably pyridyl such as 4-, 3- or 2-pyridyl.

When $R^6$ represents a non-aromatic azacycle or azabicycle, suitable values of $R^6$ include morpholinyl, piperdinyl, pyrrolidinyl, piperazinyl, methylpiperazinyl, azanorbornanyl, azabicyclo[2.2.21]octanyl and azabicyclo[3.2.2]nonyl, preferably morpholinyl, methylpiperazinyl, quinuclidinyl (azabicyclo[2.2.2]octanyl) or azabicyclo[3.2.2]nonyl.

According to a second or further aspect of the present invention, there is provided a compound of formula (Ia) or a salt or prodrug thereof:

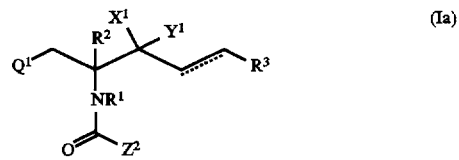

(Ia)

wherein $Q^1$ represents a phenyl group substituted by one or more halo; optionally substituted naphthyl; optionally substituted indolyl; optionally substituted benzthiophenyl; optionally substituted benzofuranyl; optionally substituted benzyl; or optionally substituted fluorenyl;

the dotted line represents an optional covalent bond;

one of $X^1$ and $Y^1$ represents H and the other represents hydroxy or $C_{1-6}$alkoxy, or $X^1$ and $Y^1$ together form a group =O or =$NOR^5$ where $R^5$ is H or $C_{1-6}$alkyl;

$R^1$ represents H or $C_{1-6}$alkyl;

$R^2$ represents H, $C_{1-6}$alkyl or $C_{2-6}$alkenyl;

$R^3$ represents phenyl optionally substituted by 1, 2, or 3 groups selected from $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ independently represent H, $C_{1-6}$alkyl, phenyl or trifluoromethyl; and $Z^2$ represents $C_{1-6}$alkyl$CO_2$H, phenyl or phenyl$C_{1-4}$alkyl, wherein each phenyl moiety is substituted by $CO_2$H.

According to a further or alternative aspect of the present invention, there is provided a compound of formula (Ib) or a salt or prodrug thereof:

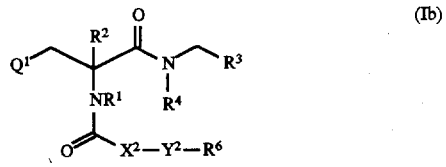

wherein $Q^1$ represents a phenyl group substituted by one or more halo, optionally substituted naphthyl, optionally substituted indolyl, optionally substituted benzthiophenyl, optionally substituted benzofuranyl, optionally substituted benzyl or optionally substituted fluorenyl;

$X^2$ represents a bond, O, S or $NR^7$;

$Y^2$ represents a bond or $C_{1-6}$alkylidene;

$R^1$ represents H or $C_{1-6}$alkyl;

$R^2$ represents H, $C_{1-6}$alkyl or $C_{2-6}$alkenyl;

$R^3$ represents phenyl optionally substituted by 1, 2, or 3 groups selected from $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ independently represent H, $C_{1-6}$alkyl, phenyl or trifluoromethyl;

$R^4$ represents H or $C_{1-6}$alkyl;

$R^5$ represents H or $C_{1-6}$alkyl; and $R^6$ represents $NR^cR^d$ (where $R^c$ and $R^d$ each independently represent H, $C_{1-6}$alkyl or phenyl$C_{0-4}$alkyl optionally substituted in the phenyl ring by one or more of $C_{1-6}$alkyl, $C_{1-6}$alkoxy, halo or trifluoromethyl) or an optionally substituted aromatic or non-aromatic azacyclic or azabicyclic group.

A particular subgroup of compounds according to the invention is represented by compounds of formula (Ic), and salts and prodrugs thereof:

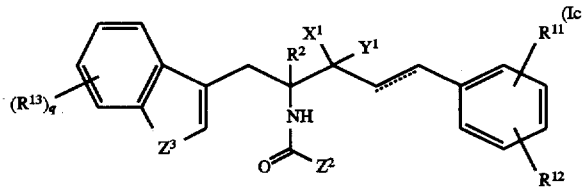

wherein $R^2$, $X^1$ and $Y^1$ are as defined for formula (I);

the dotted line represents an optional covalent bond;

$Z^2$ represents $C_{1-6}$alkyl$CO_2$H, phenyl or phenyl$C_{1-4}$alkyl, wherein each phenyl moiety is substituted by $CO_2$H;

$Z^3$ represents O, S or $NR^{14}$ (where $R^{14}$ is H, $C_{1-6}$alkyl, optionally substituted phenyl($C_{1-4}$alkyl), $CO_2R^a$ or $CONR^aR^b$, where $R^a$ and $R^b$ are as previously defined), preferably S or NH;

$R^{11}$ and $R^{12}$ each independently represent H, $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ are as previously defined;

each $R^{13}$ may occupy any available carbon atom of the bicyclic ring system and independently represents $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ are as previously defined; and q is 0, 1, 2 or 3, preferably 0.

Another particular sub-group of compounds according to the invention is represented by compounds of formula (Id), and salts and prodrugs thereof:

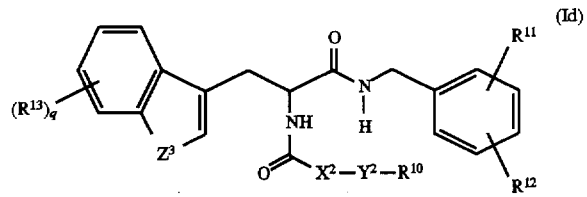

wherein $X^2$ and $Y^2$ are as defined for formula (I);

$Z^2$ represents O, S or $NR^{14}$ (where $R^{14}$ is H, $C_{1-6}$alkyl, optionally substituted phenyl($C_{1-4}$alkyl), $CO_2R^a$ or $CONR^aR^b$, where $R^a$ and $R^b$ are as previously defined), preferably S or NH;

$R^{10}$ is imidazolyl, triazolyl, tetrazolyl, oxazolyl, thiazolyl, pyrrolyl, pyrazolyl, pyrazinyl, pyridyl, oxadiazolyl, thiadiazolyl, isoxazolyl, isothiazolyl, benzimidazolyl, benzoxazolyl, indolyl, morpholinyl, piperdinyl, pyrrolidinyl, piperazinyl, methylpiperazinyl, azanorboranyl, azabicyclo[2.2.21]octanyl or azabicyclo[3.2.2]nonyl, preferably imidazolyl, pyridyl, morpholinyl, methylpiperazinyl, azabicyclo[2.2.2]octanyl or azabicyclo[3.2.2]nonyl;

$R^{11}$ and $R^{12}$ each independently represent H, $C_{1-6}$alkyl, $C_{2-6}$alkenyl, $C_{2-6}$alkynyl, chloro, bromo, fluoro, iodo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ are as previously defined;

each $R^{13}$ may occupy any available carbon atom of the bicyclic ring system and independently represents $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ are as previously defined; and q is 0, 1, 2 or 3, preferably 0.

For use in medicine, the salts of the compounds of formula (I) will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, oxalic acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Thus, for example, when $R^1$ or $R^5$ is other than H, the nitrogen atom to which it is attached may be further substituted to give a quaternary ammonium salt. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

The compounds according to the invention may exist both as enantiomers and as diastereomers. It is to be understood that all such isomers and mixtures thereof are encompassed within the scope of the present invention.

Specific compounds within the scope of the present invention include:

N-(5-(3,5-bis(trifluoromethyl)phenyl)-1-(3-indolyl)-3-pentanone-2-yl)-succinamic acid;

5-(3,5-bis(trifluoromethyl)phenyl)-2-(4-carboxybutyramido)-1-(3-indolyl)-3-pentanone;

5-(3,5-bis(trifluoromethyl)phenyl)-2-(6-carboxyhexanamido)-1-(3-indolyl)-3-pentanone;

5-(3,5-bis(trifluoromethyl)phenyl)-2-(4-carboxybenzamido)-1-(3-indolyl)-3-pentanone;

5-(3,5-bis(trifluoromethyl)phenyl)-2-(2-carboxybenzamido)-1-(3-indolyl)-3-pentanone;

5-(3,5-bis(trifluoromethyl)phenyl)-2-(3-carboxybenzamido)-1-(3-indolyl)-3-pentanone;

N-(3,5-bis(trifluoromethyl)benzyl)-2-((4-pyridyl)acetamido)-3-(3-indolyl)propionamide;

N-(3,5-bis(trifluoromethyl)benzyl)-2-((3-pyridyl)acetamido)-3-(3-indolyl)propionamide;

N-(3,5-bis(trifluoromethyl)benzyl)-N-methyl-2-(3-(3-pyridyl)propionamido)-3-(3-indolyl)propionamide;

N-(3,5-bis(trifluoromethyl)benzyl)-N-methyl-2-(4-(1-(1-azabicyclo[2.2.3]nonyl))butyramido)-3-(3-indolyl)propionamide;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are adminisitered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention further provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; epilepsy; neurodegenerative disorders such as dementia, including senile dementia of the Alzheimer type, Alzheimer's disease and Down's syndrome; demyelinating diseases such as MS and ALS and other neuropathological disorders such as peripheral neuropathy, including diabetic and chemotherapy-induced neuropathy, and postherpetic and other neuralgias; small cell carcinomas such as small cell lung cancer; respiratory diseases, particularly those associated with excess mucus secretion such as chronic obstructive airways disease, bronchopneumonia, chronic bronchitis, cystic fibrosis and asthma, and bronchospasm; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atropic dermatitis, urticaria, and other eczematoid dermatitis; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; emesis, including acute, delayed and anticipatory emesis, for example, induced by chemotherapy, radiation, toxins, pregnancy, vestibular disorders, surgery, migraine and variations in intercranial pressure; disorders of bladder function such as bladder detrusor hyper-reflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine.

The compounds of formula (I) are also of value in the treatment of a combination of the above conditions, in particular in the treatment of combined post-operative pain and post-operative nausea and vomiting.

The compounds of formula (I) are particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis and especially migraine.

The present invention further provides a compound of formula (I), or a salt or prodrug thereof, for use in therapy.

In the treatment of conditions involving actions of tachykinins released physiologically in response to noxious or other stimuli, a suitable dosage level is about 0.001 to 50 mg/kg per day, preferably about 0.005 to 10 mg/kg per day, and especially about 0.005 to 5 mg/kg per day. The compounds may be administered on a regimen of 1 to 4 times per day, preferably once daily.

According to a further or alternative aspect, the present invention provides a method of treatment of a human or animal subject suffering from or susceptible to a condition characterised by the presence of an excess of tachykinins, especially substance P, which method comprises administering to a human or animal subject in need of such treatment an effective amount of a compound of formula (I), or a salt or prodrug thereof.

The present invention also provides the use of a compound of formula (I), or a salt or prodrug thereof, for the manufacture of a medicament for the treatment of conditions characterised by the presence of an excess of tachykinins, especially substance P.

Compounds of formula (I) wherein $Z^1$ represents a group of formula (a) may be prepared from intermediates of formula (II):

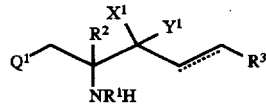

wherein $Q^1$, $R^1$, $R^2$, $R^3$, $X^1$, $Y^1$ and—are as defined for formula (I), by reaction with a reagent suitable to introduce the group $COZ^2$ where $Z^2$ represents $C_{1-6}$alkyl$CO_2H$, phenyl or phenyl$C_{1-4}$alkyl, wherein each phenyl moiety is substituted by $CO_2H$.

Suitable reagents will be readily apparent to those skilled in the art and include, for example, suitable carboxylic acid anhydrides and esters of formula $Z^2CO$—$OR^{30}$, where $R^{30}$ is alkyl, such as $C_{1-4}$alkyl, e.g. ethyl. The reaction is conducted in the presence of a base, such as a tertiary amine, for example, triethylamine, preferably in the presence of an acylation catalyst such as, for example, 4-dimethylaminopyridine. The reaction is conveniently effected in a suitable organic solvent, such as, for example, a halogenated hydrocarbon, e.g. dichloromethane, or dimethyl formamide.

Acid anhydrides and esters of formula $Z^2CO$—$OR^{30}$ are commercially available or may be prepared by conventional methods, for example, as described in the accompanying examples or in Helv. Chim. Acta, 57, 2332 (1974).

Intermediates of formula (II) wherein $X^1$ and $Y^1$ together represent =O and the double bond is present may be prepared by reaction of an aldehyde of formula $R^3CHO$ with a compound of formula (III):

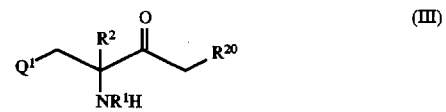

wherein $Q^1$, $R^1$ and $R^2$ are as defined for formula (I) and $R^{20}$ represents a group $PR^x_3$ or $PO(OR^x)_2$, wherein $R^x$ represents phenyl or $C_{1-10}$alkyl, in the presence of a base.

Suitable bases include alkali metal hydrides, such as, for example, sodium hydride, alkali metal carbonates, such as, for example, potassium carbonate, and strong organic bases such as, for example, 1,8-diazabicylo[5.4.0] undec-7-ene in the presence of anhydrous lithium chloride.

The reaction is conveniently effected in a suitable organic solvent, such as an ether, e.g. tetrahydrofuran, or acetonitrile, suitably at ambient temperature.

Compounds of formula (II) wherein one of $X^1$ and $Y^1$ represents H and the other represents hydroxy may be prepared from the corresponding compounds of formula (II) wherein $X^1$ and $Y^1$ together represent =O, by reduction.

Suitable reducing agents include, for example, hydride reducing agents such as lithium aluminium hydride and sodium borohydride.

The reaction is conveniently carried out in a suitable organic solvent, such as an ether, e.g. tetrahydrofuran, suitably at ambient temperature.

Compounds of formula (II) wherein one of $X^1$ and $Y^1$ represents H and the other represents $C_{1-6}$alkoxy may be prepared from the corresponding compounds of formula (II) wherein one of $X^1$ and $Y^1$ represents H and the other represents hydroxy, by alkylation.

Suitable alkylation procedures include treatment of an alcohol of formula (II) with an alkali metal hydride, such as sodium hydride, and a $C_{1-6}$alkylhalide. Suitable halides include, in particular, bromides and iodides.

The reaction is conveniently effected in an anhydrous organic solvent, for example, an ether, e.g. dimethoxyethane, suitably at ambient temperature.

Compounds of formula (II) wherein $X^1$ and $Y^1$ together represent =$NOR^5$ may be prepared from the corresponding compounds of formula (II) wherein $X^1$ and $Y^1$ together represent =O by the addition of hydroxylamine, or a derivative thereof. Compounds wherein $R^5$ is other than H may be prepared from the corresponding compounds wherein $R^5$ is H by alkylation, for example, using a diazo compound, such as diazomethane, or an alkyl halide or sulphate.

Compounds of formula (II) wherein the double bond is absent may be prepared from the corresponding unsaturated compounds of formula (II) by reduction.

Suitable reduction procedures include catalytic hydrogenation. Suitable hydrogenation catalysts include nobel metals, for example, platinum or palladium, or oxides thereof, which may be supported, for example, on charcoal. A preferred catalyst is Wilkinson's catalyst (tris (triphenylphosphine)rhodium(I)chloride).

The reaction is conveniently effected in a suitable organic solvent, such as an ether, e.g. tetrahydrofuran, an alcohol, e.g. ethanol, or an ester, e.g. ethyl acetate, suitably at ambient temperature.

Compounds of formula (III) may be prepared from compounds of formula (IV)

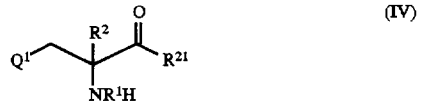

wherein $Q^1$, $R^1$ and $R^2$ are as defined for formula (I) and $R^{21}$ represents an alkoxy or a suitably substituted amino group, such as a group $NR^yOR^z$, where $R^y$ and $R^z$ represent alkyl, in particular a group $NCH_3(OCH_3)$, by reaction with a compound of formula $CH_3PO(OR^x)_2$, where $R^x$ is an alkyl group, in the presence of a base.

Suitable reaction procedures will be readily apparent to the skilled person and examples thereof are described in the accompanying Examples.

Suitable bases of use in the reaction include alkyl lithiums, such as butyl lithiums.

Compounds of formula (IV) are commercially available or may be prepared using standard procedures well known to the skilled person in the art. The compounds of formula (IV) are amino acid derivatives. Syntheses of amino acids and derivatives thereof are well documented and are described, for example, in *Chemistry and Biochemistry of the Amino Acids*, ed. G. C. Barrett, Chapman and Hall, 1985.

Compounds of formula (I) wherein $Z^1$ represents a group of formula (b) and $Z^2$ is the group $—X^2—Y^2—R^6$ wherein $X^2$ represents O, S or $NR^7$ may be prepared by reaction of intermediates of formula (V) with compounds of formula (VI):

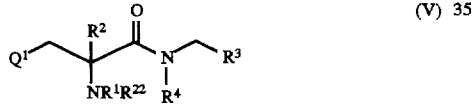

wherein $Q^1$, $R^1$, $R^2$, $R^3$, $R^4$, $R^6$, $X^2$ and $Y^2$ are as defined for formula (I), and one of $R^{22}$ and $R^{23}$ represents a group CO—A, where A represents an activating group, and the other of $R^{22}$ and $R^{23}$ represents H, in the presence of a base.

Suitable activating groups represented by A include phenoxy substituted by one or more electron-withdrawing substituents. A preferred activating group is 4-nitrophenoxy.

Suitable bases of use in the reaction include tertiary amines such as, for example, triethylamine, or dimethylaminopyridine (DMAP).

When $X^2$ represents $NR^7$, $R^{22}$ preferably represents CO—A and $R^{23}$ preferably represents H.

When $X^2$ represents O or S, $R^{22}$ preferably represents H and $R^{23}$ preferably represents CO—A.

Alternatively, compounds of formula (I) wherein $X^2$ is NH may be prepared from intermediates of formula (V) wherein $R^{22}$ is H (hereinafter intermediates (VA)) by reaction with an isocyanate of formula $R^6(CH_2)_nN=C=O$, where n is zero or an integer from 1 to 6.

The reaction is conveniently effected in a suitable organic solvent such as an ether, for example, tetrahydrofuran.

Compounds of formula (I) wherein $X^2$ represents a bond may be prepared from intermediates of formula (VA) by reaction with a reagent suitable to introduce the group $CO—X^2—Y^2—R^6$.

Suitable reagents will be readily apparent to those skilled in the art and include, for example, carboxylic acids of formula $R^6—Y^2—X^2—COOH$ and acyl halides of formula $R^6—Y^2—X^2—COHal$, where Hal is halo, such as chloro, bromo or iodo. The reaction is preferably conducted in the presence of a base, such as a tertiary amine, for example, triethylamine, conveniently in a suitable organic solvent, such as, for example, dimethyl formamide.

Compounds of formula (V) wherein $R^{22}$ is an activating group (hereinafter intermediates (VB)) may be prepared from corresponding compounds of formula (VA) by reaction with a compound of formula (VII)

wherein A represents an activating group, such as a phenyl group bearing one or more electron-withdrawing substituents, for example, 4-nitrophenyl, and Hal represents halo, such as chloro or bromo, in the presence of a base.

Suitable bases of use in the reaction include tertiary amines, such as, for example, triethylamine.

Compounds of formula (VI) wherein $R^{23}$ is an activating group may be prepared from corresponding compounds of formula (VI) wherein $R^{23}$ is H, by reaction with a compound of formula (VII) in the presence of a base, such as a tertiary amine, for example, triethylamine or DMAP.

Acids and acyl halides of formulae $R^6—Y^2—X^2—COOH$ and $R^6—Y^2—X^2—COHal$ are commercially available or may be prepared by conventional methods, for example, as described in the accompanying examples or in *Helv. Chim. Acta*, 57, 2332 (1974).

The preparation of intermediates of formula (VA) is described in WO93/01169. Thus intermediates of formula (VA) may be prepared by reaction of an amino acid of formula (VIII)

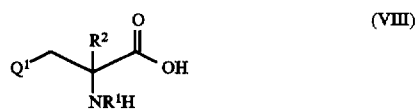

wherein $Q^1$, $R^1$ and $R^2$ are as defined for formula (I), in a suitably protected form, with an amine of formula $HNR^4—CH_2R^3$, wherein $R^3$ and $R^4$ are as defined for formula (I).

The reaction is suitably effected in the presence of a base, such as a tertiary amine, for example, triethylamine, preferably in the presence of a suitable alkylchloroformate, such as t-butylchloroformate, conveniently in a suitable organic solvent, such as a halogenated hydrocarbon, e.g. dichloromethane. Alternatively, the reaction may be effected in the presence of a coupling agent, such as dicyclohexylcarbodiimide.

Compounds of formula (VIII) are commercially available or may be prepared using standard syntheses. Syntheses of amino acids are well documented and are described, for example, in *Chemistry and Biochemistry of the Amino Acids*, ed. G. C. Barrett, Chapman and Hall, 1985.

Where the above-described processes for the preparation of the compounds according to the invention give rise to mixtures of stereoisomers, these isomers may be separated, suitably by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 29 to 30 of European Patent Specification No. EP-A-0 528 495. The compounds were found to be active with $IC_{50}$ at the NK1 receptor of less than 150 nM.

The compounds of this invention may be formulated as specifically illustrated at pages 28 to 29 of European Patent Specification No. EP-A-0 528 495.

The following non-limiting Examples illustrate the preparation of compounds according to the invention.

EXAMPLE 1

N-(5-(3,5-Bistrifluoromethylphenyl)-1-(3-indolyl)-3-ketopent-2-yl)-succinamic acid Sodium salt (a) N-Methoxy-N-methyl 2-t-butyloxycarbonylamino-3-(3-indolyl)propionamide N-α-BOC-L-tryptophan (100 g) was dissolved in dimethyl formamide (800 ml) and triethylamine (101 g) was added. The reaction was cooled to −30° C. and isobutyl chloroformate (42.5 ml) was added, maintaining the internal temperature to below −20° C. The reaction was stirred for 15 minutes before adding N,O-dimethyl hydroxylamine hydrochloride (64 g) and then diluting the reaction with dichloromethane (1 l), maintaining the internal temperature below 0° C. The reaction was stirred for 15 minutes, poured into ethyl acetate (3l) and washed with 10% citric acid (1 l), water (3×1 l), saturated sodium bicarbonate (1 l) and water (1 l). The organic phase was dried ($MgSO_4$), filtered, and evaporated until crystallisation ensued. The suspension was diluted with petroleum ether, filtered and dried to yield the title compound; mp=129°–130° C.; $^1$H NMR (360 MHz, $D_6$ DMSO) δ10.80 (1H, s); 7.51 (1H, d, J=7 Hz); 7.33 (1H, d, J=7 Hz); 7.16 (1H, s); 7.08–6.97 (3H, m); 4.62–4.58 (1H, m); 3.72 (3H, s); 3.34 (3H, s); 3.02–2.81 (2H, m); 1.31 (9H, s).

(b) 2-t-Butyloxycarbonylamino-1-(3-indolyl)-4-dimethylphosphono-3-butanone

Dimethyl methane phosphonate (205 g) was dissolved in tetrahydrofuran (800 ml), cooled to −70° C.; and then treated with n-butyllithium (1.6M in hexane, 900 ml), maintaining the internal temperature of the reaction at below −55° C. The reaction was stirred for one hour before adding the product of part (a) (90 g). The reaction was stirred at −70° C. for 30 minutes before quenching with saturated ammonium chloride. The resulting mixture was extracted with ethyl acetate and the organic extract was washed with water (5×500 ml), dried ($MgSO_4$) and evaporated. The residue was purified on silica (eluting with ethyl acetate) to yield the title compound as an oil;

$^1$H NMR (360 MHz, $CDCl_3$) δ10.84 (1H, s), 7.56 (1H, d, J=7 Hz), 7.33 (1H, d, J=7 Hz), 6.98 (1H, t, J=7 Hz), 4.34–4.31 (1H, m), 3.63 (6H, d, J=11 Hz), 3.39 (2H, d, J=22 Hz), 3.19–3.11 (1H, m), 2.91–2.84 (1H, m); found: C, 55.73, H, 6.34; N, 6.80; $C_{19}H_{27}N_2O_6P$ requires C, 55.60; H, 6.63; N, 6.82%.

(c) 5-(3,5-Bistrifluoromethylphenyl)-2-t-butyloxycarbonylamino-1-(3-indolyl)-4-penten-3-one A solution of the product of part (b) (69.0 g) in acetonitrile (600 ml) was stirred with diisopropylethylamine (43.3 g), and anhydrous lithium chloride (14.13 g) for 30 minutes before adding 3,5-bistrifluoromethylbenzaldehyde (55 g) in acetonitrile (200 ml). The reaction was stirred for two hours then the solvent was removed and the residue partitioned between ethyl acetate and water. The organic phase was washed with 10% citric acid (500 ml), water (500 ml), saturated sodium bicarbonate (500 ml) and water (500 ml). The solution was dried ($MgSO_4$), filtered and evaporated. The residue was purified by column chromatography on silica using ethyl acetate/petroleum ether (1:4) to yield the title compound as a pale yellow solid, mp=137°–138° C.; found: C, 59.23; H, 4.79; N, 5.35; $C_{26}H_{24}F_6N_2O_3$ requires C, 59.32; H, 4.60; N 5.32%.

(d) 5-(3,5-Bistrifluoromethylphenyl)-2-t-butyloxycarbonylamino-1-(3-indolyl)-3-pentanone The product of part (c) was heated under reflux with tri-n-butyltin hydride (51.12 g) in toluene for 20 hours. The reaction was cooled and purified by column chromatography on silica using ethyl acetate/petroleum ether (1:4) to yield the title compound as a white solid (37.1 g), mp=138°–140° C.: found: C, 59.23; H,4.90; N, 5.28; $C_{26}H_{24}F_6N_2O_3$ requires C, 59.09, H, 4.96; N, 5.30%.

(e) 2-Amino-5-(3,5-bistrifluoromethylphenyl)-1-(3-indolyl)-3-pentanone Hydrochloride The product of part (d) was treated with ethereal hydrogen chloride for one hour. The precipitated white solid was filtered and dried, mp=84°–86° C.; found: C,54.40; H, 4.25; N, 6.10; $C_{21}H_{18}F_6N_2O$. HCl requires C, 54.26; H, 4.12; N, 6.03%.

(f) N-(5-(3,5-Bistrifluoromethylphenyl)-1-(3-indolyl)-3-ketopent-2-yl)-succinamic acid Sodium salt To a mixture of the compound of part (e) (215 mg) and dichloromethane (3 ml) cooled to −78° C. under argon, was added with stirring dry triethylamine (70 μl). To the resulting solution was added succinic anhydride (50 mg) and 4-dimethylaminepyridine (5 mg), and the mixture was allowed to warm to room temperature. The mixture was stirred at room temperature for a further 3 hours before pouring into aqueous 2N hydrochloric acid (4 ml). The organic layer was separated, and the aqueous layer extracted with ethyl acetate. The combined organic layers were dried ($MgSO_4$) and evaporated. The residue was treated with one equivalent of aqueous sodium hydroxide, sufficient acetonitrate added to render the mixture homogeneous, and the resulting solution freeze dried. The resulting solid was dissolved in ethyl acetate (1 ml) and petroleum ether (10 ml) added. The mixture was boiled to half volume, and the solid product collected by filtration, and dried in-vacuo to afford the title compound. $^1$N NMR (360 MHz; $D_6$-DMSO) δ2.15 (2H, m), 2.25 (2H, m), 2.72 (1H, m), 2.87 (4H, m), 3.05 (1H, dd, J=5.7, 14.5 Hz), 4.42 (1H, m), 6.97 (1H, t, J=7.8 Hz), 7.05 (1H, t, J=8.0 Hz), 7.18 (1H, d, J=2.2 Hz), 7.32 (1H, d, J=8.3 Hz), 7.48 (1H, d, J=7.7 Hz), 7.79 (2H, s), 7.85 (1H, s), 9.00 (1H, d, J=6.8 Hz), 10.90 (1H, s); m/e (CI$^+$) 528 (MH$^+$). Found: C, 52.12; H, 3.99; N, 4.67. $C_{25}H_{21}F_6N_2O_4Na.1.5$ ($H_2O$) requires C, 52.00; H, 4.19; N, 4.85%.

EXAMPLE 2

5-(3,5-Bistrifluoromethylphenyl)-2-(4-carboxybutyramido)-1-(3-indolyl)-3-pentanone To a solution of ethyl hydrogen glutarate (0.27 g) in dimethylformamide (10 ml) at 0° C., under an atmosphere of nitrogen, was added 1-(3-dimethylaminopropyl)-3-ethylcarbodiimide hydrochloride (0.32 g). After stirring for 1 hour dichloromethane (10 ml) was added followed by triethylamine (0.15 ml) and the compound of Example 1(e) (0.5 g). After stirring for 16 hours the mixture was diluted with ethyl acetate, washed with water (3×), dried and concentrated. After purification by chromatography on silica gel (eluant ethyl acetate-petroleum ether 1:1) the reaction product was dissolved in tetrahydrofuran (5 ml) and water (2 ml) and treated with lithium hydroxide hydrate (100 mg) for 16 hours. The solution was diluted with ethyl acetate, washed with 2N HCl, dried and concentrated. The residue in acetonitrile (5 ml) was treated with 1N NaOH (0.9 ml) and freeze dried to give the sodium salt of the title compound. $^1$N NMR (360 MHz, D$_6$-DMSO) δ10.88 (1H, s), 8.30 (1H, d, J=7.0 Hz), 7.86 (1H, s), 7.80 (2H, s), 7.49 (1H, d, J=7.8 Hz), 7.32 (1H, d, J=8.1 Hz), 7.13 (1H, s), 7.06 (1H, t, J=7.0 Hz), 6.97 (1H, t, J=7.9 Hz), 4.50 (1H, m), 3.10–2.66 (6H, m), 2.13–2.06 (4H, m), 1.67–1.61 (2H, m). m/e 543 ([M+H]$^+$, Cl$^+$).

EXAMPLE 3

5-(3,5-Bistrifluoromethylphenyl)-2-(6-carboxyhexanamido)-1-(3-indolyl)-3-pentanone The sodium salt of the title compound was prepared by the method of Example 2 using ethyl hydrogen pimalate. $^1$N NMR (360 MHz, D$_6$-DMSO) δ11.04 (1H, s), 8.20 (1H, d, J=7.2 Hz), 7.86 (1H, s), 7.83 (2H, s), 7.49 (1H, d, J=7.8 Hz), 7.32 (1H, d, J=8.0 Hz), 7.12 (1H, s), 7.05 (1H, t, J=7.0 Hz), 6.96 (1H, t, J=6.9 Hz), 4.49 (1H, m), 3.10–2.70 (6H, m), 2.06–2.01 (4H, m), 1.39–1.35 (4H, m), 1.11–1.05 (2H, m). m/e 571 ([M+H]$^+$, Cl$^+$).

EXAMPLE 4

4-(3,5-Bistrifluoromethylphenyl)-2-(4-carboxybenzamido)-1-(3-indolyl)-3-pentanone The sodium salt of the title compound was prepared by the method of Example 2 using methyl terephthalate. Mp 272°–274° C.; $^1$H NMR (360 MHz, D$_6$-DMSO) δ10.84 (1H, s), 8.81 (1H, s), 7.95 (2H, d, J=8.2 Hz), 7.86 (3H, s), 7.78 (2H, d, J=8.2 Hz), 7.57 (1H, d, J=7.8 Hz), 7.32 (1H, d, J=8.1 Hz), 7.19 (1H, d, J=2.2 Hz), 7.06 (1H, t, J=7.0 Hz), 6.98 (1H, t, J=7.2 Hz), 4.73 (1H, m), 3.35–3.22 (2H, m), 3.13–2.84 (4H, m). m/e 577 ([M+H]$^+$, Cl$^+$).

EXAMPLE 5

5-(3,5-Bistrifluoromethylphenyl)-2-(2-carboxybenzamido)-1-(3-indolyl)-3-pentanone To a suspension of phthalic anhydride (0.16 g) and the compound of Example 1(e) (0.5 g) in dichloromethane (10 ml) under nitrogen was added triethylamine (0.15 ml) and 4-dimethylaminopyridine (5 mg). After stirring for 16 hours 2N hydrochloric acid was added and extracted with dichloromethane. The dichloromethane solution was dried, concentrated and the residue purified by chromatography on silica eluting with 10% methanol/dichloromethane. Crystallisation from diethyl ether/petroleum ether gave the title compound, mp 154°–157° C.; $^1$N NMR (360 MHz, D$_6$-DMSO) δ10.88 (1H, s), 7.84 (1H, s), 7.81 (2H, s), 7.62 (1H, d, J=6.6 Hz), 7.52–7.49 (2H, m), 7.39–7.27 (4H, m), 7.06 (1H, t, J=7.9 Hz), 6.98 (1H, t, J=7.9 Hz), 4.55 (1H, m), 3.14–3.07 (2H, m), 2.92–2.75 (4H, m). m/e 577 ([M+H]$^+$, Cl$^+$).

EXAMPLE 6

5-(3,5-Bistrifluoromethylphenyl)-2-(3-carboxybenzamido)-1-(3-indolyl)-3-pentanone Prepared by the method of Example 2 using monobenzyl isophthalate with the exception that cleavage of the intermediate ester was effected by stirring in methanol-formic acid over palladium black under an atmosphere of nitrogen for 16 hours. The mixture was filtered, concentrated, chromatographed on silica gel (10% methanol/dichloromethane) and crystallised from diethyl ether/petroleum ether to give the title compound, mp 113°–116° C.; $^1$N NMR (360 MHz, D$_6$-DMSO) δ10.88 (1H, s), 8.42 (1H, s), 8.07 (1H, d, J=7.7 Hz), 7.97 (1H, d, J=7.8 Hz), 7.59–7.51 (2H, m), 7.32 (1H, d, J=8.1 Hz), 7.18 (1H, d, J=2.2 Hz), 7.06 (1H, t, J=7.0 Hz), 6.98 (1H, t, J=7.0 Hz), 4.74 (1H, m), 3.35–3.22 (2H, m), 3.14–2.80 (4H, m). m/e 577 ([M+H]$^+$, Cl$^+$).

EXAMPLE 7

N-(3,5-Bis(trifluoromethyl)benzyl)-2-((4-pyridyl)acetamido)-3-(3-indolyl)propionamide a) N-(3,5-Bis(trifluoromethyl)benzyl)-2-amino-3-(3-indolyl) propionamide Hydrochloride N-α-BOC-L-Tryptophan (12.6 g) and triethylamine (8.36 g) were dissolved in dichloromethane, cooled to −10° C., and treated with isobutylchloroformate. The reaction was stirred for 15 minutes before adding 3,5-bistrifluoromethylbenzylamine (10 g), and stirring for 30 minutes at 0° C. The solvent was removed and the residue was taken up into ethyl acetate and washed with 10% citric acid (100 ml), saturated sodium bicarbonate solution (100 ml) and water (100 ml). The organic phase was dried (MgSO$_4$) filtered and evaporated. The residue was dissolved in methanolic hydrogen chloride and stirred for 48 hours. The solvent was removed to yield the title compound (14.11 g).

b) N-(3,5-Bis(trifluoromethyl)benzyl)-2-((4-pyridyl)acetamido)-3-(3-indolyl)propionamide A suspension of 4-pyridylacetic acid (465 mg) in dichloromethane (10 ml) was treated with carbonyldiimidazole (245 mg) and triethylamine (0.42 ml) for 1.5 hours. The compound of Example 7a) (465 mg) in dimethylformamide (5 ml) was added and the solution was stirred for 3 hours then diluted with ethyl acetate, washed with sodium bicarbonate solution, dried (Na$_2$SO$_4$) and concentrated. The residue was crystallised from ethyl acetate-diethyl ether to give the title compound, mp 227° C.; found: C, 58.84; H, 4.04; N, 9.95. C$_{27}$H$_{22}$F$_6$N$_4$O$_2$ requires C, 59.12; H, 4.04; N, 10.21.

EXAMPLE 8

N-(3,5-Bis(trifluoromethyl)benzyl)-2-((2-pyridyl)acetamido)-3-(3-indolyl)propionamide Prepared by the method of Example 7 using 2-pyridylacetic acid. Mp 190°–193° C.; found C, 59.31; H, 4.05; N, 10.12. C$_{27}$H$_{22}$F$_6$O$_2$N$_4$ requires C, 59.13; H, 4.03; N, 10.22.

EXAMPLE 9

N-(3,5-Bis(trifluoromethyl)benzyl)-N-methyl-2-(3-(3-pyridyl)propionamido)-3-(3-indolyl)propionamide a) N-(3,5-Bis(trifluoromethyl)benzyl)-N-methyl-2-amino-3-(3-indolyl)propionamide Prepared by the method of Example 7(a) using N-methyl-3,5-bis(trifluoromethyl)benzylamine (prepared by dissolving 3,5-bis(trifluoromethyl)benzyl bromide in methanolic methyl amine solution)

b) N-(3,5-Bis(trifluoromethyl)benzyl)-N-2-(3-(3-indolyl)-propionamido)-3-(3-indolyl)-propionamide 3-(3-Pyridyl acetic acid) (0.15 g), 1-[3-dimethylaminopropyl]-3-ethylcarbodiimide hydrochloride (0.24 g) and hydroxybenzotriazole (0.14 g) were stirred together in dimethyl formamide (5 ml) for two hours. The product of Example 9(a) (0.4 g) was added, followed by triethylamine (0.5 ml). The reaction was diluted with dichloromethane (5 ml) and stirred for 16 hours. The reaction was diluted with ethyl acetate (50 ml) and washed with saturated sodium bicarbonate, and brine (5×50 ml), dried (MgSO$_4$), filtered, and evaporated to yield an oil, purified by column chromatography on silica using dichloromethane/methanol (99:1) to yield the title compound, mp 172°–174° C.; found: C, 60.42; H, 4.55; N, 9.72. $C_{29}H_{26}F_6N_4O_2$ requires C, 60.76; H, 4.47; N, 9.86%.

EXAMPLE 10

N-(3,5-Bis(trifluoromethyl)benzyl)-N-methyl-2-(4-(1-(1-azabicyclo[2.2.3]nonyl))butyramido)-3-(3-indolyl)propionamide Prepared by the method of Example 9 using 4-(1-(1-azabicyclo[2.2.3]nonyl))butyric acid, mp 140°–142° C.; found: C, 61.16; H, 5.79; N, 8.61. $C_{33}H_{38}F_6N_4O_2 \cdot \frac{1}{2}H_2O$ requires C, 61.39; H, 6.09; N, 8.68%.

We claim:

1. A compound of formula (Ia) or a salt or prodrug thereof:

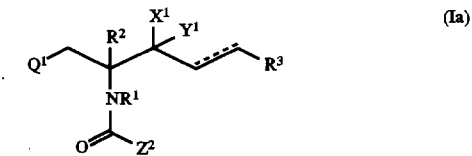

wherein $Q^1$ represents optionally substituted indolyl;

the dotted line represents an optional covalent bond;

one of $X^1$ and $Y^1$ represents H and the other represents hydroxy or $C_{1-6}$alkoxy, or $X^1$ and $Y^1$ together form a group =O or =NOR$^5$ where R$^5$ is H or $C_{1-6}$alkyl;

$R^1$ represents H or $C_{1-6}$alkyl;

$R^2$ represents H, $C_{1-6}$alkyl or $C_{2-6}$alkenyl;

$R^3$ represents phenyl optionally substituted by 1,2, or 3 groups selected from $C_{1-6}$alkyl, $C_{2-6}$alkenyl, $C_{2-6}$alkynyl, halo, cyano, nitro, trifluoromethyl, trimethylsilyl, OR$^a$, SR$^a$, SOR$^a$, NR$^a$R$^b$, NR$^a$COR$^b$, NR$^a$CO$_2$R$^b$, CO$_2$R$^a$ or CONR$^a$R$^b$, where R$^a$ and R$^b$ independently represent H, $C_{1-6}$alkyl, phenyl or trifluoromethyl; and $Z^2$ represents $C_{1-6}$alkylCO$_2$H, phenyl or phenylC$_{1-4}$alkyl, wherein each phenyl moiety is substituted by CO$_2$H.

2. A compound as claimed in claim 1 of formula (Ic), or a salt or prodrug thereof:

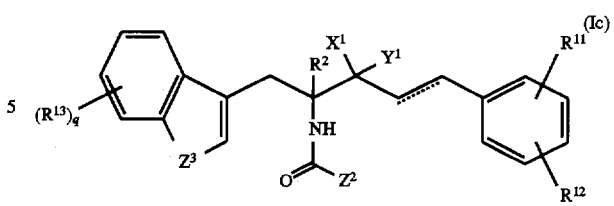

wherein $R^2$, $X^1$ and $Y^1$ are as defined for formula (I);

the dotted line represents an optional covalent bond;

$Z^2$ represents $C_{1-6}$alkylCO$_2$H, phenyl or phenylC$_{1-4}$alkyl, wherein each phenyl moiety is substituted by CO$_2$H;

$Z^3$ represents NR$^{14}$ (where R$^{14}$ is H, $C_{1-6}$alkyl, optionally substituted phenyl ($C_{1-4}$alkyl), CO$_2$R$^a$ or CONR$^a$R$^b$, where R$^a$ and R$^b$ are as previously defined), R$^{11}$ and R$^{12}$ each independently represent H, $C_{1-6}$alkyl, $C_{2-6}$alkenyl, $C_{2-6}$alkynyl, halo, cyano, nitro, trifluoromethyl, trimethylsilyl, OR$^a$, SR$^a$, SOR$^a$, NR$^a$R$^b$, NR$^a$COR$^b$, NR$^a$CO$_2$R$^b$, CO$_2$R$^a$ or CONR$^a$R$^b$, where R$^a$ and R$^b$ are as previously defined;

each R$^{13}$ may occupy any available carbon atom of the bicyclic ring system and independently represents $C_{1-6}$alkyl, $C_{2-6}$alkenyl, $C_{2-6}$alkynyl, halo, cyano, nitro, trifluoromethyl, trimethylsilyl, OR$^a$, SR$^a$, SOR$^a$, NR$^a$R$^b$, NR$^a$COR$^b$, NR$^a$CO$_2$R$^b$, CO$_2$R$^a$ or CONR$^a$R$^b$, where R$^a$ and R$^b$ are as previously defined; and q is 0, 1, 2 or 3.

3. A compound as claimed in claim 1 wherein R$^1$ represents H or methyl.

4. A compound as claimed in claim 1 wherein R$^2$ represents H or methyl.

5. A compound as claimed in claim 1 wherein R$^3$ represents phenyl substituted by 1, 2 or 3 groups selected from nitro, trifluoromethyl, trimethylsilyl, bromo, chloro, fluoro, iodo, cyano, methyl, ethyl, cyclopropyl, vinyl, methoxy, phenoxy and amino.

6. A compound as claimed in claim 5 wherein R$^3$ represents 3,5-bis(trifluoromethyl)phenyl.

7. A compound as claimed in claim 1 wherein the double bond is absent.

8. A compound as claimed in claim 1 wherein X$^1$ and Y$^1$ together represent =O.

9. A compound as claimed in claim 1 wherein Z$^2$ represents the group $C_{1-3}$alkylCO$_2$H or phenyl substituted in the para position by CO$_2$H.

10. A pharmaceutical composition comprising a compound as claimed in claim 2 in association with a pharmaceutically acceptable carrier.

11. A method for the treatment or prevention of physiological disorders associated with an excess of tachykinins, which method comprises administration to a patient in need thereof of a tachykinin reducing amount of a compound according to claim 1, or a pharmaceutically acceptable salt or prodrug thereof, or a composition comprising a compound according to claim 2, or a pharmaceutically acceptable salt or prodrug thereof.

12. A method according to claim 11 for the treatment or prevention of pain or inflammation.

13. A method according to claim 11 for the treatment or prevention of migraine.

14. A method according to claim 11 for the treatment or prevention of emesis.

15. A compound selected from

N-(5-(3,5-bis(trifluoromethyl)phenyl)-1-(3-indolyl)-3-pentanone-2-yl)succinamic acid;

5-(3,5-bis(trifluoromethyl)phenyl)-2-(4-carboxybutyramido)-1-(3-indolyl)-3-pentanone;

5-(3,5-bis(trifluoromethyl)phenyl)-2-(6-carboxyhexanamido)-1-(3-indolyl)-3-pentanone;

5-(3,5-bis(trifluoromethyl)phenyl)-2-(4-carboxybenzamido)-1-(3-indolyl)-3-pentanone;

5-(3,5-bis(trifluoromethyl)phenyl)-2-(2-carboxybenzamido)-1-(3-indolyl)-3-pentanone;

5-(3,5-bis(trifluoromethyl)phenyl)-2-(3-carboxybenzamido)-1-(3-indolyl)-3-pentanone;

or a salt or prodrug thereof.

* * * * *